US005824864A

United States Patent [19]
Fox et al.

[11] Patent Number: 5,824,864
[45] Date of Patent: Oct. 20, 1998

[54] MAIZE GENE AND PROTEIN FOR INSECT CONTROL

[75] Inventors: Timothy W. Fox, Des Moines; Carl W. Garnaat, Ankeny; Terry EuClaire Meyer, Urbandale, all of Iowa

[73] Assignee: Pioneer Hi-Bred International, Inc., Des Moines, Iowa

[21] Appl. No.: 449,986

[22] Filed: May 25, 1995

[51] Int. Cl.⁶ .......................... C12N 15/00; C12N 15/29; C12N 15/82; A01H 5/00
[52] U.S. Cl. .................... 800/205; 536/23.6; 435/172.3; 435/252.3; 435/419
[58] Field of Search ........................ 536/23.6; 424/93 A; 435/172.3, 240.4, 252.3, 419; 800/205

[56] References Cited

U.S. PATENT DOCUMENTS

| | | | |
|---|---|---|---|
| 4,522,803 | 6/1985 | Lenk et al. | 424/1.1 |
| 4,588,578 | 5/1986 | Fountain et al. | 424/1.1 |
| 5,034,322 | 7/1991 | Rogers et al. | 435/172.3 |
| 5,071,654 | 12/1991 | English | 424/405 |
| 5,157,207 | 10/1992 | Carlson et al. | 800/200 |
| 5,234,834 | 8/1993 | Fischer et al. | 435/320.1 |
| 5,252,348 | 10/1993 | Schreier et al. | 424/450 |

FOREIGN PATENT DOCUMENTS

| | | | |
|---|---|---|---|
| 2090552 | 8/1994 | Canada | C12N 15/82 |
| WO 93/22441 | 11/1993 | WIPO | C12N 15/53 |
| WO 94/21805 | 9/1994 | WIPO | C12N 15/82 |
| WO 95/01098 | 1/1995 | WIPO | A01N 63/00 |

OTHER PUBLICATIONS

Saczynska, et al., "Effects of pH and detergents on galactolipase activity in chloroplasts of chilling–sensitive and chilling resistant plant", *ACTA Physiologiae Plantarum*, vol. 16, No. 4, 1994:317–328.
Andrews et al. (1988) Characterization of the lipid acyl hydrolase activity of the major potato (*Solanum tuberosum*) tuber protein, patatin, by cloning and abundant expression in a baculovirus vector, *Biochem. J.*, 252:199–206.
Berry–Lowe, et al. (1982) The nucleotide sequence, expression, and evolution of one member of a multigene family encoding the small subunit of ribulose–1,5–bisphosphate carboxylase in soybean, *Journal of Molecular and Applied Genetics*, vol. 1, No. 6, pp. 483–498.
Bogusz, et al. (1990) Nonlegume hemoglobin genes retain organ–specific expression in heterologous transgenic plants, *The Plant Cell*, vol. 2, pp. 633–641.
Boulter et al. (1989) Use of cowpea trypsin inhibitor (CpTI) to protect plants against insect predation, *Biotech. Adv.*, vol. 7, pp. 489–497.
Broadway et al. (1986) Plant proteinase inhibitors: mechanism of action and effect on the growth and digestive physiology of larval *heliothis zea* and *spodoptera exiqua*, *J. Insect Physiol.*, vol. 32, No. 10, pp. 827–833.

Cashmore, A.R. (1983) Nuclear Genes Encoding the Small Subunit of RIbulose–1,5–Bisphosphate Carboxylase, *Genetic Engineering of Plants, an Agricultural Perspective*, pp. 29–38.
Coruzzi, et al. (1983) Nucleotide Sequences of Two Pea cDNA Clones Encoding the Small Subunit of Ribulose 1,5–Bisphosphate Carboxylase and the Major Chlorophyll a/b–binding Thylakoid Polypeptide, *The Journal of Biological Chemistry*, vol. 258, pp. 1399–1402.
Czapla et al. (1990) Effect of Plant Lectins on the larval Development of European Corn Borer (Lepidoptera: Pyralidae) and Southern Corn Rootworm (Coleoptera: Chrysomelidae) *Journal of Economic Entomology*, vol. 83, No. 6, pp. 2480–2485.
Dunsmuir et al. (1983) The Major Chlorophyll a/b Binding Protein of Petunia is Composed of Several Polypeptides Encoded by a Number of Distinct Nuclear Genes, *Journal of Molecular and Applied Genetics*, 2:285–300.
Galliard, T. (1971) The enzymic deacylatin of phospholipids and galactolipids in plants, *Biochem. J.*, 121:379–390.
Ganal et al. (1991) Genetic and Physical Mapping of the Patatin Genes in Potato and Tomato, *Mol. Gen. Genet.*, 225:501–509.
Gatehouse et al. (1986) The effects of a–Amylase Inhibitors on Insect Storage Pests: Inhibition of a–Amylase in vitro and Effects on Development in vivo. *J. Sci. Food Agric.*, 37:727–734.
Hirel et al. (1992) Forcing expression of a soybean root glutamine synthetase gene in tobacco leaves induces a native gene encoding cytosolic enzyme, *Plant Molecular Biology*, 20:207–218.
Hofgen et al. (1990) Biochemical and Genetic Analysis of Different Patatin Isoforms Expressed in Various Organs of Potato (*Solanum Tuberosum*), *Plant Science*, 66:221–230.
Ishimoto et al. (1989) Growth inhibitory effects of an a–amylase inhibitor from the kidney bean, *phaseolus vulgaris*(L.) on three species of brochids (coleoptera: bruchidae), *App. Ent. Zool*,24:(3): 281–286.
Keller et al. (1991) Vascular–Specific Expression of the Bean GRP 1.8 Gene is Negatively Regulated, *The Plant Cell*, vol. 3, pp. 1051–1061.
Leach et al. (1991) Promoter analysis of the highly expressed rolC and rolD root–inducing genes of *Agrobacterium rhizogenes*: enhancer and tissue–specific DNA determinants are dissociated, *Plant Science*, vol. 79, pp. 69–76.
Miao et al. (1991) Ammonia–Regulated Expression of a Soybean gene Encoding Cytosolic Glutamine Synthetase in Transgenic Lotus Corniculatus, *The Plant Cell*, vol. 3, 11–22.

(List continued on next page.)

*Primary Examiner*—Douglas W. Robinson
*Assistant Examiner*—Thomas Haas

[57] ABSTRACT

Nucleotide sequences encoding a maize 5C9 polypeptide, the 5C9 polypeptide and structural and functional equivalents, and methods for controlling insect infestation in plants are provided.

27 Claims, 4 Drawing Sheets

OTHER PUBLICATIONS

Mignery et al. (1984) Isolation and Sequence analysis of cDNAs for the Major Potato Tuber Protein, patatin, *Nucleic Acids Research*, vol. 12, No. 21, pp. 7987–8001.

Mignery et al. (1988) Molecular characterization of the patatin multigene family of potato, *Gene*, 62:27–44.

Murdock et al. (1990) Biological effects of plant lectins on the cowpea weevil, Phytochemistry, vol. 29, No. 1, pp. 85–89.

Racusen, David (1986) Esterace specificity of patatin from two potato cultivars[1], *Can. J. Bot.*, vol. 64, pp. 2104–2106.

Racusen, David (1984) Lipid acyl hydrolase of patatin[1], *Can. J. Bot.*, vol. 62, pp. 1640–1644.

Rosahl et al. (1987) Expression of a Tuber–Specific Storage Protein in Transgenic Tobacco Plants: Demonstration of an Esterase Activity, *The EMBO Journal*, vol. 6, No. 5, pp. 1155–1159.

Sanger et al. (1990) Characteristics of a strong promoter from figwort mosaic virus: comparison with the analogous 35S promoter from cauliflower mosaic virus and the regulated mannopine synthase promoter, *Plant Molecular Biology*, 14:433–443.

Shukle et al. (1983) Lipoxygenase, Trypsin Inhibitor, and Lectin from Soybeans, Effects on Larval Growth of *Manduca sexta* (Lepidoptera: Sphingidae)[1], *Environmental Entomology*, vol. 12, No. 3, pp. 787–791.

Steikema et al. (1988) Molecular Cloning and Analysis of Four Potato Tuber mRNAs, *Plant Molecular Biology*, 11:255–269.

Teeri et al. (1989) Gene fusions to lacZ reveal new expression patterns of chimeric genes in transgenic plants, *The EMBO Journal*, vol. 8, No. 2, pp. 343–350.

Vancanneyt et al. (1989) Expression of a Patatin–like Protein in the Anthers of Potato and Sweet Pepper Flowers, *The Plant Cell*, vol. 1, 533–540.

Weiss et al. (1994) Isolation of cDNAs encoding guanine nucleotide–binding protein β–subunit homologues from maize (ZGB1) and Arabidopsis (AGB1), *Proc. Natl. Acad. Sci. USA*, vol. 91, pp. 9554–9558.

```
   1  GAATTCGGCA CGAGCACACA CAAGCGAGGA GCACTACCTG TTGGTTGGAT
  51  TCTCTTCAGT CTAGCTACTC GATCGGTCCC TTGTCCACAG TTAAGTTTCA
 101  GACACATGGG GAGCATTGGC AGAGGCACGG CCAACTGCGC CACCGTGCCG
 151  CAGCCGCCGC CGTCGACAGG GAAGCTCATC ACGATCCTGA GCATCGATGG
 201  CGGCGGCATC CGCGGCCTTA TCCCGGCGAC CATCATTGCG TACCTCGAGG
 251  CCAAGCTCCA GGAGCTGGAC GGCCCGGACG CTCGGATCGC CGACTACTTC
 301  GATGTGATTG CCGGGACGAG CACCGGCGCC CTGCTCGCGT CGATGCTGGC
 351  GGCGCCGGAC GAGAACAACC GGCCGCTGTT CGCCGCCAAG GACCTCACCA
 401  CGTTCTACCT CGAGAACGGC CCAAAGATCT CCCACAGAA AAAGGCTGGG
 451  TTGCTGACGC CGCTGAGGAA CCTGCTGGGC CTGGTGCGGG GCCCCAAGTA
 501  CGACGGCGTG TTCCTGCACG ACAAGATCAA GAGCCTGACG CACGACGTCA
 551  GGGTGGCGGA CACGGTGACC AACGTCATCG TGCCGGCGTT CGACGTCAAG
 601  TACCTGCAGC CCATCATCTT CTCGACGTAC GAGGCCAAGA CCGACACCCT
 651  CAAGAACGCG CACCTCTCCG ACATCTGCAT CAGCACGTCG GCGGCGCCCA
 701  CCTACTTCCC GGCGCACTTC TTCAAGACCG AGGCCACCGA CGGCCGGCCC
 751  CCCCGCGAGT ACCACCTCGT GGACGGCGGC GTCGCGGCCA ACAACCCCAC
 801  CATGGTCGCC ATGTCCATGC TCACCAAGGA GGTGCACCGC CGCAACCCCA
 851  ACTTCAACGC CGGCAGCCCC ACCGAGTACA CCAACTACCT CATCATCTCC
 901  GTCGGCACCG GGTCGGCAAA GCAGGCGGAG AAGTACACCG CGGAGCAGTG
 951  CGCGAAGTGG GGCCTCATCC AGTGGCTCTA CAACGGCGGC TTCACGCCGA
1001  TCATCGACAT CTTCTCGCAT GCCAGTTCCG ACATGGTTGA CATCCATGCG
1051  TCGATCCTCT TTCAGGCCCT GCACTGCGAG AAGAAGTACC TTCGCATCCA
1101  GGATGATACT TTGACTGGGA ACGCATCGTC CGTGGACATC GCCACCAAGG
1151  AGAACATGGA GTCTCTGATA TCGATCGGCC AGGAGCTGCT CAAGAAGCCA
1201  GTGGCGAGAG TGAACATCGA CACAGGGGTG TACGAGTCCT GCGACGGTGA
1251  GGGCACAAAT GCACAGTCGC TAGCTGACTT CGCCAAGCAA CTCTCTGACG
1301  AGCGCAAGCT ACGCAAGAGC AATCTCAACT CCAACTAATA AATACCTCTC

1351  TCAGTCACAG CATGTGCTCT TTCTGCAGAT TCACCGTTTC TTATTTTTAA
1401  TTTCAATTTC AATTCAGTGT ATGTGCGTGT GTGTGTGACT GTACTGTGTG
1451  TACCAATAAA CATTTAAGTT CAATCATTTG CTTGTCTATG ATCAAAAGAA
1501  CCATTTCCTT CTGAAAAAAA AACGGCACGA G
```

FIG.1

```
  1  MGSIGRGTAN  CATVPQPPPS  TGKLITILSI  DGGGIRGLIP  ATIIAYLEAK
 51  LQELDGPDAR  IADYFDVIAG  TSTGALLASM  LAAPDENNRP  LFAAKDLTTF
101  YLENGPKIFP  QKKAGLLTPL  RNLLGLVRGP  KYDGVFLHDK  IKSLTHDVRV
151  ADTVTNVIVP  AFDVKYLQPI  IFSTYEAKTD  TLKNAHLSDI  CISTSAAPTY
201  FPAHFFKTEA  TDGRPPREYH  LVDGGVAANN  PTMVAMSMLT  KEVHRRNPNF
251  NAGSPTEYTN  YLIISVGTGS  AKQAEKYTAE  QCAKWGLIQW  LYNGGFTPII
301  DIFSHASSDM  VDIHASILFQ  ALHCEKKYLR  IQDDTLTGNA  SSVDIATKEN
351  MESLISIGQE  LLKKPVARVN  IDTGVYESCD  GEGTNAQSLA  DFAKQLSDER
401  KLRKSNLNSN
```

MAIZE GENE AND PROTEIN FOR INSECT CONTROL

FIELD OF THE INVENTION

The present invention relates to the field of plant molecular biology. More specifically, the invention relates to isolated maize nucleotide sequences encoding an insecticidal polypeptide, and methods for control of insect infestation in plants.

BACKGROUND

The use of natural products, including proteins, is a well known method of controlling many insect pests. For example, endotoxins of *Bacillus thuringiensis* (*B.t.*) are used to control both lepidopteran and coleopteran insect pests. Genes producing these endotoxins have been introduced into and expressed by various plants, including cotton, tobacco, tomato, and maize. There are, however, several economically important insect pests that are not susceptible to *B.t.* endotoxins, including the boll weevil, *Anthonomus grandis*, and corn rootworm (CRW), *Diabrotica spp*. In addition, having other, different gene products for control of insects which are susceptible to *B.t.* endotoxins is critical for resistance management.

Several other known insecticidal proteins are found in plants. These include lectins, amylase inhibitors, and protease inhibitors, which can affect insect growth and development when ingested at high levels. See, e.g., Boulter et al., 1989; Broadway and Duffey, 1986, Czapla and Lang, 1990; Gatehouse et al., 1986. Heusing et al., 1991; Ishimoto and K. Kitamura, 1989, Murdock et al., 1990; Shuckle and Murdock, 1993. However, these proteins apparently do not provide the acute mortality afforded by *B.t.* proteins.

Patatins are a family of proteins found in potato (see Gaillaird, 1971; Racusen, 1984; Andrews et al., 1988) and other plants, particularly in solanaceous plants (Ganal et al., 1991; Vancanneyt et al., 1989). In potato the patatins are found primarily in tubers, but also at much lower levels in other plant organs (Hofgen and Willmitzer, 1990). Genes that encode patatins have been isolated. See, e.g., Mignery et al., 1984; Mignery et al., 1988; Stiekema et al., 1988. Roshal et al., 1987, transferred a patatin gene to tobacco and expressed patatin in transgenic tobacco plants.

Although the benefits of expression of heterologous genes in transgenic plants cannot be minimized, there are additional benefits to be gained from discovering native or autologous genes, the copy number of which and/or the expression of which can be increased. In addition, even when a heterologous gene is inserted into and expressed in transgenic plants, if that gene is isolated from a somewhat more closely related species, its expression level may be higher than in instances where genes from unrelated species are used, and its expression product may be more effective. Therefore, an effective insect control protein from an agronomic crop species is highly desirable.

SUMMARY

It is therefore an object of the present invention to provide isolated maize nucleotide sequences showing some sequence similarity to, but that are not substantially homologous to, genes encoding patatins and the proteins encoded thereby. It is a further object of this invention to provide expression cassettes, useful in the transformation of plant cells, that contain the isolated maize nucleotide sequences encoding the proteins of the invention.

It is also an object of the present invention to provide methods for controlling insect infestation of plants. In one aspect of the invention this comprises providing an effective amount of the insecticidal polypeptide 5C9 for ingestion by the insect. This may be accomplished by providing an insecticidally effective amount of the protein into the environment of the insects, for example by spraying or other application techniques, or by providing plant-colonizing microorganisms that have been transformed to express the isolated nucleotide sequences of the invention and which are introduced to the plant, express such gene, and provide an insecticidally effective amount of the protein.

Alternatively, the method may be effected by genetically transforming the plant to express either additional, insecticidally effective levels of the native insecticidal protein (in instances where the transformed plant is a maize plant), or to express insecticidally effective levels of the heterologous insecticidal protein (in instances where the transformed plant is other than a maize plant). The method of the invention further envisions specifically increasing the expression of the active 5C9 protein in maize by increasing its copy number and/or replacing its promoter with an over-expressing promoter, such as a constitutive or a tissue specific promoter.

In addition, the present invention also provides the method of controlling insect infestation in plants by imparting insect resistance to plants of taxons susceptible to infestation. Fertile, insect resistant plants from sexually compatible taxa that have been transformed with DNA encoding the 5C9 polypeptide of the invention, are selected and sexually crossed with a plant from the infestation-susceptible taxon. Reproductive material is recovered from the progeny of the cross, and insect resistant plants are grown up from that reproductive material. To impart resistance in taxa consisting of substantially homozygous plants the method further comprises repetitive backcrossing of the insect resistant progeny with substantially homozygous, infestation-susceptible plants from the taxon, and selecting for expression of insect resistance along with any other desired characteristics of the susceptible taxon from among the progeny of the backcross, until the desired percentage of the characteristics of the susceptible taxon are present in the progeny, along with insect resistance.

Alternatively, the invention also envisions the screening of maize plants for mutants having altered expression patterns of 5C9 such that protection against insects or other plant pathogens is increased in tissues in which 5C9 is not normally expressed, or in tissues in which expression does not occur at such effective levels.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from the following detailed description.

BRIEF DESCRIPTION OF THE DRAWINGS

FIG. 1 is the sequence (SEQ ID NO:1) of the isolated maize cDNA sequence encoding the 5C9 polypeptide.

FIG. 2 is the deduced amino acid sequence (SEQ ID NO:2) of the 5C9 polypeptide.

FIG. 3 is a schematic of 5C9 genomic and cDNA inserts.

FIG. 4 is a plasmid map of the pPHP5379 plasmid, containing the 5C9 cDNA.

DETAILED DESCRIPTION

The present invention provides isolated maize nucleotide sequences encoding a 5C9 polypeptide, the polypeptide itself, and methods for controlling insect infestation in plants using the nucleic acids and protein of the invention.

As used herein, the term "controlling insect infestation" means reducing the number of insects that cause reduced beneficial plant yield. The reduction of insect numbers can occur either through mortality, retardation of larval development (stunting), or reduced reproductive efficiency, or a combination thereof. As used herein, the terms "insecticidal" means capable of reducing the number of insects which cause reduced beneficial yield. This reduction of insect number can, again, occur through mortality, retardation of larval development (stunting),or reduced reproductive efficiency, or a combination thereof.

As used herein, the term "nucleotide sequence" means a DNA or RNA molecule or sequence, and can include, for example, a cDNA, genomic DNA, or synthetic DNA sequence, a structural gene or a fragment thereof, or an mRNA sequence, that encodes an active or functional polypeptide.

By "transgenic plant" is meant any plant or plant cell that has become transformed by the introduction, through stable and heritable incorporation, into the subject plant or plant cell, of either native DNA that is under the control of a promoter other than the promoter that typically drives expression of that DNA in a wild-type plant, and that has been introduced back into the host plant, or foreign DNA, i.e. DNA encoding for a protein not normally found within that plant species.

"Plantlet" refers to a plant sufficiently developed to have a shoot and a root that is asexually reproduced by cell culture.

"Explant" refers to a section or piece of tissue from any part of a plant for culturing.

The term "callus" and its plural "calli", refer to an unorganized group of cells formed in response to cutting, severing, or other injury inflicted on plant tissue. Excised pieces of plant tissue and isolated cells can be induced to form callus under the appropriate culture conditions. Callus can be maintained in culture for a considerable time by transferring or subculturing parts of the callus to fresh medium at regular intervals. The transfer of callus to liquid medium leads to dispersion of the tissue and the formation of a plant cell suspension culture. Callus can be induced to undergo organized development to form shoots and roots.

"Embryoid" refers to a structure similar in appearance to a plant zygotic embryo.

"Somatic hybrid" and "somatic hybridization" refers generally to stable combination of cellular material, be it protoplast/protoplast or protoplast/cytoplast combinations, and includes cybrids and cybridization.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" or a "promoter" is a DNA regulatory region capable of binding RNA polymerase in a cell and initiating transcription of a downstream (3' direction) coding sequence. For purposes of defining the present invention, the promoter sequence is bound at its 3' terminus by the translation start codon (ATG) of a coding sequence and extends upstream (5' direction) to include the minimum number of bases or elements necessary to initiate transcription. Within the promoter sequence will be found a transcription initiation site, as well as protein binding domains responsible for the binding of RNA polymerase. Eucaryotic promoters will often, but not always, contain "TATA" boxes and "CAT" boxes. Procaryotic promoters can contain Shine-Dalgarno sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of undergoing transformation, by an autologous or an exogenous DNA sequence.

A cell has been "transformed" by autologous or exogenous DNA when such DNA has been introduced inside the cell membrane. The DNA may or may not be integrated into (covalently linked to) chromosomal DNA making up the genome of the transformed cell. In procaryotes and yeasts, for example, the DNA may be maintained on an episomal element, such as a plasmid. With respect to eucaryotic cells, a stably transformed cell is one in which the DNA has become integrated into the chromosome so that it is inherited by daughter cells through chromosome replication. This stability is demonstrated by the ability of the eucaryotic cell to establish cell lines or clones comprised of a population of daughter cells containing the DNA.

A "clone" is a population of cells derived from a single cell or common ancestor by mitosis. A "cell line" is a clone of a primary cell that is capable of stable growth in vitro for many generations.

Two DNA, RNA or polypeptide sequences are "substantially homologous" or "structurally equivalent" when at least about 85% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., *Molecular Cloning, A Laboratory Manual*, Cold Spring Harbor Laboratory, New York (1982); Brown T. A., *Gene Cloning: An Introduction* (2d Ed.), Chapman & Hall, London (1990).

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacterium. Another example of a heterologous coding sequence is a construct where the coding sequence itself is not found in nature (e.g., synthetic sequences having codons different from the native gene). "Heterologous" DNA also refers to DNA not found within the host cell in nature. Allelic variation or naturally occurring mutational events do not give rise to a heterologous region of DNA, as these terms are used herein. "Native", "autologous" or "endogenous" DNA, as used herein, refer to DNA that is typically present in the host in nature.

The term "polypeptide" as used herein is used in its broadest sense, i.e., any polymer of amino acids (dipeptide or greater) linked through peptide bonds. Thus, the term "polypeptide" includes proteins, oligopeptides, protein fragments, analogues, fusion proteins and the like. The term also encompasses amino acid polymers as described above that include additional non-amino acid moieties. Thus, the term "polypeptide" includes glycoproteins, lipoproteins, phosphoproteins, metalloproteins, nucleoproteins, as well as other conjugated proteins. The term "polypeptide" contemplates polypeptides as defined above that are recombinantly produced, isolated from an appropriate source, or synthesized.

Insecticidally effective amounts of the 5C9 polypeptide can be effectively applied to infested plants by spray, dust or other formulation common in the art. This can be achieved by spraying or dusting with appropriate compositions comprising insecticidally effective amounts of the 5C9 protein in an appropriate carrier, as necessary, taking into account the environmental conditions at and around the time of application, the location and extent of insect infestation, and the like. The 5C9 protein for such application can be produced in bacterial or plant bioreactors capable of expressing large amounts of active protein that can be purified to the extent necessary and prepared for such application.

Alternatively, the peptide can be incorporated into the tissues of a susceptible plant so that in the course of infesting the plant the insects will be exposed to insecticidally effective amounts of the peptide. Known methods of doing this are to incorporate the peptide in a non-phytotoxic carrier which is adapted for systemic administration to the susceptible plants, such as an endophytic bacterium or a lipid vesicle or microsphere.

See, for example, U.S. Pat. No. 5,157,207, issued Oct. 20, 1992 to Carlson, et al., the disclosures of which are hereby incorporated by reference, directed to modified plants containing bacterial inoculants. According to the '207 patent, certain types of microorganisms, such as hybrid agricultural-chemical-producing endosymbiotic microorganisms, can colonize the interior of plants and provide useful agricultural chemicals, such as pesticides, to the plants. Certain microbial endophytes are capable of inducing enhanced resistance in a host to phytopathogens. The bacteria that are suitable for use in such a method in this invention belong to a species of bacteria that is capable of replicating in the interior tissues of a plant and of producing the desired compound of this invention. Under normal field conditions, the bacterium does not ordinarily inhabit the seed or the plant into which the bacterium is introduced. Such a bacterium can be a gram-positive bacterium, a gram-negative bacterium or a species of actinomycetes. The bacterium is modified by genetic engineering techniques to incorporate the gene coding for the compound of this invention. In a preferred embodiment, the bacterial cell is a genetically modified species of either Corynebacteria, Clavibacter, Pseudomonas, Xanthomonas or Erwinia, the Corynebacteria and clavibacters being as defined in Davis M. J. et al. (1984), loc. cit. In a particularly preferred embodiment, the bacterial cell is a strain of *Clavibacter xyli*. In a most preferred embodiment, the bacterial cell is a *Clavibacter xyli* subspecies cynodontis.

Reference also may be had to U.S. Pat. No. 5,252,348, issued Oct. 12, 1993 and directed to "Artificial viral envelopes", the disclosures of which are also hereby incorporated herein by reference. According to the '348 patent, lipid vesicles of the patent can be used to transfer biological material to plant cells.

Further reference may be had to U.S. Pat. No. 5,071,654, issued Dec. 10, 1991, the disclosures of which are hereby incorporated by reference and which are directed to insecticidal compositions involving a phospholipid vesicle with insect midgut brush border and a *Bacillus thuringiensis* protein endotoxin incorporated therein and an agriculturally-acceptable carrier. Such phospholipid vesicle compositions are stated to provide a vehicle for the application of delta endotoxin to plants. The vesicles are stated to act in much the same fashion as liposomes do in vertebrates, to facilitate the delivery of the toxins to the target midgut cells in susceptible insects.

Reference may also be had to U.S. Pat. No. 5,034,322, issued Jul. 23, 1991 to Rogers, et. al., the disclosures of which are hereby incorporated by reference and which are directed to chimeric genes suitable for expression in plant cells, but which discusses methods capable of inserting the chimeric genes of this invention into plant cells, although the reported transformation efficiencies achieved to date by such methods have been low. Discussed methods include use of lipid vesicles, also called liposomes, from which DNA may be taken up by plant cells.

Still further reference may be had to U.S. Pat. No. 4,588,578, issued May 13, 1986 to Fountain, et. al. and directed to monophasic vesicles for delivery of antimicrobials and other compounds to plants, and U.S. Pat. No. 4,522,803, issued Jun. 11, 1985 to Lenk, et. al. and directed, inter alia, to methods for treatment of infections in plants, comprising administering stable plurilamellar vesicles containing a compound effective for treating said infection. The disclosures of these patents are also hereby incorporated by reference.

The foregoing and similar methods are commonly employed with insecticidal materials which are designed to attack chewing insects and are well within the purview of one of ordinary skill in the art of insecticide and larvicide formulation and are fully contemplated in the practice of this invention. However, genes which code for the peptides of this invention can be readily synthesized using automated methods, cloned, inserted into an appropriate expression cassette, and introduced directly into cells of a susceptible plant species. Accordingly, an especially preferred embodiment of this method involves inserting into the genome of the plant a DNA sequence coding for the polypeptide of this invention in proper reading frame, together with transcription initiator and promoter sequences active in the plant. Transcription and translation of the DNA sequence(s) under control of the regulatory sequences can cause expression of the polypeptide sequence(s) at levels which provide an insecticidally effective amount of the polypeptide(s) in the tissues of the plant which are normally infected by the pests.

With a working knowledge of conventional techniques for cloning, DNA isolation, amplification and purification, for enzymatic reactions involving DNA ligase, DNA polymerase, restriction endonucleases and the like, and various separation techniques known and commonly employed by those skilled in the art (See, for example, R. Wu, ed. (1979) *Meth. Enzymol.* 68; R. Wu et al., eds. (1983) *Meth. Enzymol.* 100, 101: L. Grossman and K. Moldave, eds. (1980) *Meth. Enzymol.* 65: J. H. Miller (1972) Experiments in Molecular Genetics; R. Davis et al. (1980) *Advanced Bacterial Genetics*; R. F. Schleif and P. C. Wensink (1982) *Practical Methods in Molecular Biology*; and T. Manniatis et al. (1982) *Molecular Cloning.*), one of ordinary skill can employ any suitable gene construct containing the structural genes coding for the peptides of this invention.

The nucleotide sequence which when expressed imparts insecticidal activity is a structural gene which codes for the polypeptide of this invention, or its structural and functional equivalents. Given the amino acid sequence provided herein, any of several translationally equivalent synthetic DNA sequences can then be prepared which code for the sequence of amino acids using commercially available software, such as PC Gene™ or GCG™, and this synthetic sequence can be inserted into an appropriate plant expression cassette.

In carrying out this invention, it will be appreciated that numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong promoter sequence at one end to causes the gene to be transcribed at a higher frequency, and a poly-A recognition sequence at the other end for proper processing and transport of the messenger RNA. An example of a preferred (empty) expression cassette into which the DNA sequence of the present invention can be inserted is the pPH1414 plasmid developed by Beach et al. of Pioneer Hi-Bred International, Inc., Johnston, Iowa. Preferred plant expression cassettes can be designed to include one or more selectable marker genes, including, for example, kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as selectable markers to identify and separate transformed cells. Preferred selection agents include, for example, kanamycin, chlorosulfuron, phosphonothricin, hygromycin and methotrexate, and preferred markers are genes conferring resistance to these compounds. A cell in which the foreign genetic material in a vector is functionally expressed has been "transformed" by the vector and is referred to as a "transformant". A "foreign" gene refers to any gene introduced into a plant by transformation techniques, and can include autologous genes re-introduced into the plant species from which the gene or nucleotide sequence was isolated. Typically such autologous genes will have been put under the control of a promoter different from the promoter that is operably linked to the autologous gene in a wild type plant.

A particularly preferred vector is a plasmid, by which is meant a circular double-stranded DNA molecule that is not a part of the chromosomes of the cell.

As mentioned above, genomic, synthetic and cDNA representing the 5C9 gene and encoding the 5C9 polypeptide may be used in this invention. The vector of interest may also be constructed partially from a cDNA clone, partially from a synthetic sequence and/or partially from a genomic clone. When the 5C9 gene sequence is in hand, genetic constructs are made which contain the necessary regulatory sequences to provide for efficient expression of the gene in the host cell. According to this invention, the genetic construct will contain a genetic sequence coding for the 5C9 polypeptide and one or more regulatory sequences operably linked on either side of the nucleotide sequence encoding the 5C9 polypeptide. Typically, the regulatory sequences will be selected from the group comprising of promoters and terminators. The regulatory sequences may be from autologous or heterologous sources.

Promoters that may be used in the genetic sequence include, for example, nos, ocs, phaseolin, caMV, FMV, ubiquitin and other promoters isolated from the DNA of plants or other sources, both natural and synthetic. A tissue-specific promoter can be used in instances where it may be desirable to localize production of the 5C9 expression product to a particular tissue type.

An efficient plant promoter that may be used is an overproducing plant promoter. Overproducing plant promoters that may be used in this invention include the promoter of the small sub-unit (ss) of the ribulose-1, 5-bisphosphate carboxylase from soybean (Berry-Lowe et al., *J. Molecular and App. Gen.*, 1:483–498 (1982)), and the promoter of the chlorophyll a-b binding protein. These two promoters are known to be light-included in eukaryotic plant cells (see, for example, *Genetic Engineering of Plants, An Agricultural Perspective*, Cashmore, Pelham, New York, 1983, pp. 29–38, G. Coruzzi et al., *J. Biol. Chem.*, 258:1399 (1983), and P. Dunsmuir, et al., *J. Molecular and App. Gen.*, 2:285 (1983)) and may be particularly desirable in the practice of the present invention. An especially preferred constitutive promoter is the 35S promoter from Cauliflower Mosaic Virus.

Root-specific promoters are also known and can be selected from the many available from the literature or isolated de novo from various compatible species. For example, Hirel, B., Marsolier, M. C., Hoarau, A., Hoarau, J., Brangeon, J., Schafer, R., and Verma, D. P. S., *Plant Molecular Biology*, October, 1992. v. 20 (2), pp. 207–218, describe a root-specific glutamine synthetase gene from soybean. Keller, B. and Baumgartner, C., *The Plant Cell*, October, 1991, v. 3 (10), pp. 1051–1061, describe a root-specific control element in the GRP 1.8 gene of French bean. Sanger, M., Daubert, S., and Goodman, R. M., *Plant Molecular Biology*, March, 1990, v. 14 (3), pp. 433–443, discuss the root-specific promoter of the Mannopine Synthase (MAS) gene of *Agrobacterium tumefaciens*. Miao, G. H., Hirel, B., Marsolier, M. C., Ridge, R. W., and Verma, D. P. S., *The Plant Cell*, January, 1991, v. 3 (1), pp. 11–22, describe a full-length cDNA clone encoding cytosolic glutamine synthetase (GS), which is expressed in roots and root nodules of soybean. Bogusz, D., Llewellyn, D. J., Craig, S., Dennis, E. S., Appleby, C. A., and Peacock, W. J., *The Plant Cell*, July, 1990, v. 2(7), pp. 633–641, discusses two root-specific promoters isolated from hemoglobin genes from the nitrogen-fixing nonlegume *Parasponia andersonii* and the related non-nitrogen-fixing nonlegume *Trema tomentosa*. The promoters of these genes were linked to a beta-glucuronidase reporter gene and introduced into both the nonlegume *Nicotiana tabacum* and the legume *Lotus corniculatus*, and in both instances root-specific promoter activity was preserved. Leach, F. and Aoyagi, K., *Plant Science* (Limerick) 1991, 79 (1):69–76, describe their analysis of the promoters of the highly expressed ro1C and ro1D root-inducing genes of *Agrobacterium rhizogenes*. They concluded that enhancer and tissue-specific DNA determinants are dissociated in those promoters. Teeri, T. H., Lehvaslaiho, H., Franck, M., Uotila, J., Heino, P., Palva, E. T., Montagu, M. van, and Herrera-Estrella, L., *EMBO Journal*, 1989, 8 (2):343–350, used gene fusions to lacZ to show that the Agrobacterium T-DNA gene encoding octopine synthase is especially active in the epidermis of the root tip and that the TR2' gene was root specific in the instant plant and stimulated by wounding in leaf tissue, an especially desirable combination of characteristics for use with an insecticidal or larvicidal gene. The TR1' gene, fused to NPTII, (neomycin phosphotransferase II) showed similar characteristics.

Various promoters particularly useful in plants are disclosed and discussed in U.S. Pat. No. 5,234,834 (Fischer et al., Aug. 10, 1993). Fischer et al. also discuss expression cassette and vector construction useful for plant genetic applications.

The expression cassette comprising the nucleotide sequence coding for the 5C9 polypeptide operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotyic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli*, *S. typhimurium*, and *S. marcescens*. Eukaryotic hosts such as yeast or filamentous fungi may also be used in this invention.

The isolated cloning vector will then be introduced into the plant cell using any convenient technique, including, for example, chemically induced uptake, electroporation, liposomes, retroviruses, electrophoresis, microparticle bombardment, and microinjection into cells from any plant species, including monocotyledonous or dicotyledonous plants, in cell or tissue culture or in whole plants where applicable, to provide transformed plant cells or plants containing as foreign DNA at least one copy of the DNA sequence of the plant expression cassette. Using known techniques, protoplasts can be regenerated and cell or tissue culture can be regenerated to form whole fertile plants which tarry and express the desired gene for the selected protein. See generally Chapters 6, 7 and 9 in Glick and Thompson, *Methods in Plant Molecular Biology and Biotechnology*, CRC Press, Boca Raton, 1993.

It will also be appreciated by those of ordinary skill that the plant vectors provided herein can be incorporated into *Agrobacterium tumefaciens*, which can then be used to transfer the vector into susceptible plant cells. Thus, this invention provides a method for insect control in *Agrobacterium tumefaciens*-susceptible plants in which the expression cassette is introduced into the cells by infecting the cells with *Agrobacterium tumefaciens*, a plasmid of which has been modified to include a plant expression cassette which expresses 5C9 in the manner of this invention.

The invention envisions transformation of both monocotyledonous and dicotyledonous species of plants. Preferred monocot species include, for example, maize, sorghum, wheat, and rice. Preferred dicots include, for example, soybeans, sunflowers, rapeseed (for example, canola), and peanuts. These monocots and dicots can be transformed using microprojectile bombardment methods that have been widely published. Other monocot species, such as Asparagus, and many of the dicot species listed above, as well as sunflower, alfalfa, tobacco, cotton and tomato can be transformed using an Agrobacterium species such as *Agrobacterium rhizogenes* or *Agrobacterium tumefaciens*.

This invention also provides methods of imparting resistance to insects to plants of a susceptible taxon comprising culturing regenerable cells or tissues from at least one plant from the taxon, introducing into the cells of the cell or tissue culture at least one copy of an expression cassette comprising a gene which codes for the polypeptide of this invention, operably linked to plant regulatory sequences which cause the expression of peptide(s) in the cells, and regenerating insect resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the structural gene for the 5C9 polypeptide and associated regulatory sequences via crossing and backcrossing. Such intermediate methods will further comprise sexually crossing the insect-resistant plant with a plant from the infestation-susceptible taxon, recovering reproductive material from the progeny of the cross, and growing insect-resistant plants from the reproductive material. Where desirable or necessary, the agronomic characteristics of the susceptible taxon can be substantially preserved by expanding this method to include the further steps of repetitively backcrossing the insect-resistant progeny with infestation-susceptible plants from the susceptible taxon, and selecting for expression of insecticidal activity (or an associated marker gene) among the progeny of the backcross, until the desired percentage of the characteristics of the susceptible taxon are present in the progeny along with the gene imparting insecticidal activity.

The following description further exemplifies the compositions of this invention and the methods of making and using them. However, it will be understood that other methods, known by those of ordinary skill in the art to be equivalent, can also be employed.

EXAMPLE 1

Generation of 5C9 cDNA

A subtracted maize tassel cDNA library was constructed for the isolation of tissue specific genes. Weiss et al., Isolation of cDNAs Encoding Guanine Nucleotide-binding Protein β-submit Homologues From Maize (ZGB1) and Arabidopsis (AGBI), P.N.A.S. 91:9554–9558, 1994. Individual clones were transferred to microtiter plates, in glycerol stocks. Clones were selected at random and used to probe Northern blots using Enhanced Chemiluminescence (ECL) system from Amersham. An ECL labeled probe of approximately 0.6 kb hybridized only with approximately 1.9 kb mRNA from tassels at different developmental stages.

A second tassel cDNA library was screened with the approximately 0.6 kb probe and two more cDNA clones were isolated. Restriction digest analysis indicated that plasmid pPHP5379 contains nearly full length coding sequence for 5C9.

A maize genomic library constructed from inbred line A632, was probed with inserts from pPHP5379, and two overlapping clones, 5C9.5 and 5C9.10, were isolated and purified. Restriction digest analysis and subcloning of genomic fragments from 5C9.5 were performed, in pPHP5827 and pPHP5828, with XbaI genomic fragment into pSKII plus in both orientations, and pPHP5530, Bam HI/NotI genomic fragment into pKSII plus.

Another Northern membrane was probed with $^{32}$P labeled 5C9. After 24 hours exposure, high levels of hybridization signal was visible with mRNA from premeiotic stage tassels, as well as from 7 day post-pollinated kernels, and lesser signal was detected with meiotic stage tassels, quartet stage tassels and uninucleate stage tassels. The hybridization signal was barely detectable with mRNA from binucleate stage tassels, 21 day post-pollinated kernels, 14 day post-pollinated kernels, and from 12 cm long ear shoot. After 90 hours exposure, signal was faintly detectable with mRNA from 6 day seedling green leaves, 6 day old seedling roots, and from ear shoots.

EXAMPLE 2

Protein Expression in Plants

Transgenic plants can be produced using any of several art-recognized methods. See, generally, Glick and Thompson, *Methods in Plant Molecular Biology and Biotechnology*, CRC Press, Boca Raton, 1993. For example, microprojectile bombardment can be utilized to transform maize callus, and whole, stably transformed plants regenerated therefrom. Such plants are transformed with a cDNA or genomic DNA or synthetic DNA sequence coding for the 5C9 polypeptide or a structural equivalent, operably linked to an over-producing promoter that drives expression of the polypeptide, either constitutively or in a tissue specific manner. Such plants are then tested for resistance to insect infestation using art-recognized techniques.

A plant expression cassette, employing the regulatory sequences developed by Beach, et al., and containing the 5C9 protein gene, is constructed. This plasmid contains an enhanced 35S promoter spanning nucleotides −421 to +2 of Cauliflower Mosaic Virus with the region from −421 to −90 duplicated in tandem, a 79 bp HindIII Sal1 fragment from pJII1101 spanning the 5' leader sequence of Tobacco Mosaic Virus, a 579 bp fragment spanning the first intron from maize AdH1-S, and a 281 bp fragment spanning the poly-adenylation site from the nopaline synthase gene in pTiT37. Alternative promoters, for example the ubiquitin promoter or the wheat Ta peroxidase promoter, and including tissue specific promoters, can also be utilized.

Another construct that can be used as an expression cassette differs from pPHI414 in that it lacks the AdH intron segment. However, like pPHI414, it is constructed to have numerous restriction sites between the O' segment and the NOS segment, which sites can be conveniently used for splicing any desired protein structural gene into position.

The vector can be cotransformed with a similar plasmid containing a selectable marker, for example a marker for antibiotic or herbicide resistance, into Black Mexican Sweet corn protoplasts using art recognized transformation methods, for example electroporation or microprojectile bombardment. These protoplasts can then be induced to regenerate cell walls and develop into callus by conventional techniques. Likewise, this callus can then be subjected to selection to select for transformed colonies, and these colonies can be tested for expression of protein with antisera for the appropriate protein using known methods. The efficiency of protection can be measured by infesting callus (or suspension cultures derived from callus) with the target insect and measuring survival percentages.

The protein gene can be introduced into embryogenic maize callus and other tissues by methods similar to those used for Black Mexican Sweet. A particularly preferred transformation method is microprojectile bombardment. Embryogenic callus of numerous elite lines has been regenerated to produce whole fertile plants. When normal integration of the transgene occurs, the insect resistance imparted by the endogenous production of the protein can be expected to be simply inherited, dominant trait and can therefore be introduced into other plant varieties of the species by simple crossing or backcrossing if desired.

Using the foregoing techniques, the gene that codes for the 5C9 protein of this invention can be introduced into maize cells, and the expression of protein in such cells can be determined by transient assays.

All publications and patents mentioned in this specification are hereby incorporated herein by reference.

What is claimed is:

1. An isolated DNA molecule having the nucleotide sequence shown in FIG. 1 (SEQ ID No. 1) or a structural equivalent thereof which hybridizes to SEQ ID No. 1 under high stringency and encodes a polypeptide retaining the insecticidal actiivty of 5C9.

Figure 2:
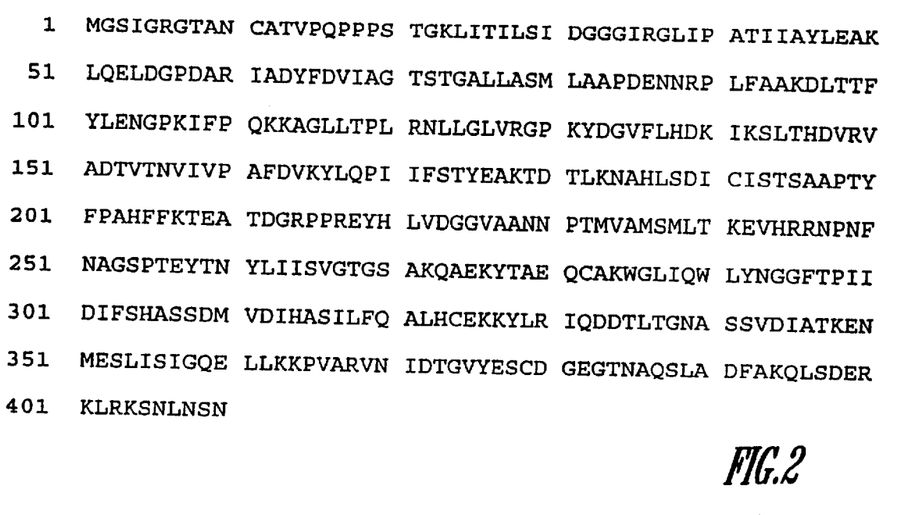
Figure 3:
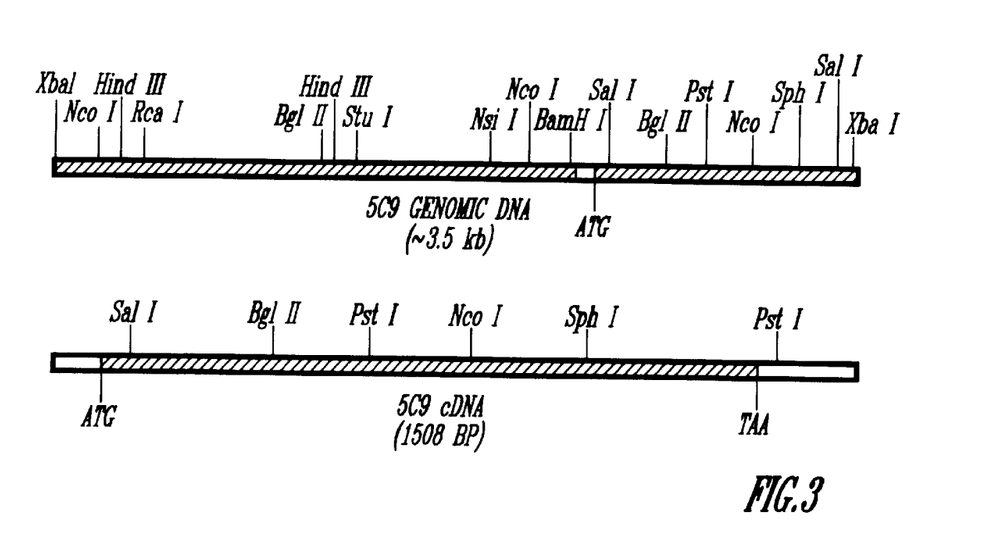
Figure 4:
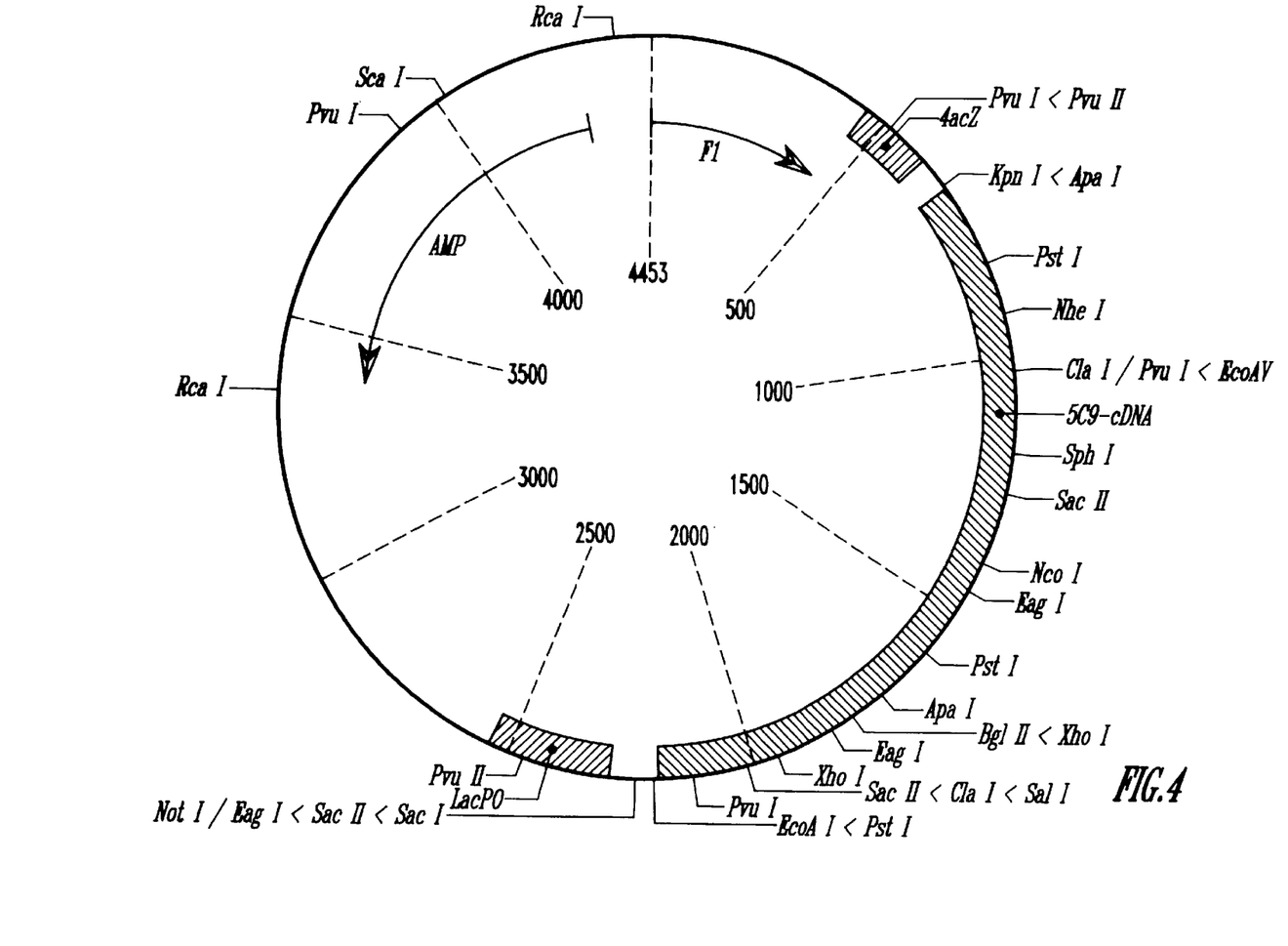

2. An isolated polynucleotide encoding the amino acid sequence of the 5C9 polypeptide, said polypeptide having the amino acid sequence shown in FIG. 2 (SEQ ID NO:2).

3. A polynucleotide according to claim 2, wherein said polynucleotide is a RNA molecule.

4. A polynucleotide according to claim 2, wherein said polynucleotide is a DNA molecule.

5. An expression cassette comprising the DNA of claim 1, operably linked to one or more regulatory sequences not naturally associated with said DNA and that cause the expression of the DNA in plants.

6. Transformed plant cells comprising at least one expression cassette according to claim 5.

7. Transformed plant cells according to claim 6, further characterized as being cells of a monocotyledonous species.

8. Transformed plant cells according to claim 7, further characterized as being maize, sorghum, wheat, or rice cells.

9. Transformed plant cells according to claim 6, further characterized as being cells of a dicotyledonous species.

10. Transformed plant cells according to claim 9, further characterized as being cells soybean, alfalfa, rapeseed, tobacco, sunflower, cotton, or tomato cells.

11. A maize cell or tissue culture comprising cells according to claim 8.

12. A transformed plant comprising transformed plant cells containing at least one copy of the expression cassette of claim 5.

13. An expression cassette comprising the DNA of claim 1, operably linked to one or more bacterial expression regulatory sequences that cause the expression of the DNA in bacterial cells.

14. Bacterial cells comprising, as a foreign plasmid, at least one copy of an expression cassette of claim 13.

15. A method of controlling insect infestation of a plant comprising providing an insecticidally effective amount of the polypeptide encoded by the polynucleotide of claim 2.

16. The method of claim 15 wherein the polypeptide is provided by plant-colonizing microorganisms which produce the polypeptide after the microorganisms are applied to the plant.

17. The method of claim 15 wherein the polypeptide is provided by expression of a polynucleotide encoding the polypeptide, the polynucleotide having been incorporated in the plant by the previous genetic transformation of a parent cell of the plant.

18. A method of controlling insect infestation of a plant comprising inserting into the genome of the plant a polynucldotide according to claim 2, in proper reading frame relative to transcription initiator and promoter sequences active in plants, to cause expression of the polynucleotide at levels that provide an insecticidally effective amount of 5C9 polypeptide in the tissues of the plant that are normally affected by the insects.

19. The method of claim 18 wherein the plant is a monocotyledonous species.

20. The method of claim 19 wherein the plant is a species selected from the group consisting of maize, wheat, rice, and sorghum.

21. The method of claim 18 wherein the plant is a dicotyledonous species.

22. The method of claim 21 wherein the plant is a species selected from the group consisting of soybean, alfalfa, sunflower, safflower, rape, tobacco, cotton, and tomato.

23. The method of claim 18, further comprising culturing cells or tissues from the plant, introducing into the cells of the cell or tissue culture by a transformation method at least one or more copies of an expression cassette of claim 6 are present, and regenerating whole plants from the cell or tissue culture.

24. The method of claim 23 further comprising sexually or clonally reproducing the whole plant so that at least one copy of the sequence provided by the expression cassette is present in the cells of progeny of the reproduced plant.

25. A method of controlling insect infestation of a plant by imparting insect resistance to plants of a taxon susceptible to infestation, the method comprising selecting a fertile insect resistant plant prepared by the method of claim 24 from a sexually compatible taxon, sexually crossing the insect resistant plant with a plant from the infestation-susceptible taxon, recovering reproductive material from the progeny of the cross, and growing insect resistant plants from the reproductive material.

26. The method of claim 25 for imparting insect resistance in a taxon further comprising repetitively crossing the insect resistant progeny with infestation-susceptible plants from the taxon, and selecting for expression of insect resistance along with any other desired characteristics of the susceptible taxon from among the progeny of the cross, until the desired percentage of the characteristics of the susceptible taxon are present in the progeny along with insect resistance.

27. A method of controlling insect infestation of a plant comprising inserting into the genome of the plant a DNA according to claim 1, in proper reading frame relative to transcription initiator and promoter sequences active in plants, to cause expression of the DNA at levels that provide an insecticidally effective amount of 5C9 polypeptide in the tissues of the plant that are normally affected by the insects.

* * * * *

UNITED STATES PATENT AND TRADEMARK OFFICE
CERTIFICATE OF CORRECTION

PATENT NO. : 5,824,864
DATED : Oct. 20, 1998
INVENTOR(S) : Timothy W. Fox, et al.

It is certified that error appears in the above-identified patent and that said Letters Patent is hereby corrected as shown below:

Column 17, Line 35, should read--
  nucleotide according to claim 2, in proper reading frame   --.

Column 18, Line 12, should read--
  one or more copies of an expression cassette of claim 5 are Signed and Sealed this Twenty-third Day of March, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1531 base pairs
        ( B ) TYPE: nucleic acid
        ( C ) STRANDEDNESS: single
        ( D ) TOPOLOGY: linear (ii) MOLECULE TYPE: DNA (genomic)

(xi) SEQUENCE DESCRIPTION: SEQ ID NO:1:

| | | | | | | |
|---|---|---|---|---|---|---|
| GAATTCGGCA | CGAGCACACA | CAAGCGAGGA | GCACTACCTG | TTGGTTGGAT | TCTCTTCAGT | 60 |
| CTAGCTACTC | GATCGGTCCC | TTGTCCACAG | TTAAGTTTCA | GACACATGGG | GAGCATTGGC | 120 |
| AGAGGCACGG | CCAACTGCGC | CACCGTGCCG | CAGCCGCCGC | CGTCGACAGG | GAAGCTCATC | 180 |
| ACGATCCTGA | GCATCGATGG | CGGCGGCATC | CGCGGCCTTA | TCCCGGCGAC | CATCATTGCG | 240 |
| TACCTCGAGG | CCAAGCTCCA | GGAGCTGGAC | GGCCCGGACG | CTCGGATCGC | CGACTACTTC | 300 |
| GATGTGATTG | CCGGGACGAG | CACCGGCGCC | CTGCTCGCGT | CGATGCTGGC | GGCGCCGGAC | 360 |
| GAGAACAACC | GGCCGCTGTT | CGCCGCCAAG | GACCTCACCA | CGTTCTACCT | CGAGAACGGC | 420 |
| CCAAAGATCT | TCCCACAGAA | AAAGGCTGGG | TTGCTGACGC | CGCTGAGGAA | CCTGCTGGGC | 480 |
| CTGGTGCGGG | GCCCCAAGTA | CGACGGCGTG | TTCCTGCACG | ACAAGATCAA | GAGCCTGACG | 540 |
| CACGACGTCA | GGGTGGCGGA | CACGGTGACC | AACGTCATCG | TGCCGGCGTT | CGACGTCAAG | 600 |
| TACCTGCAGC | CCATCATCTT | CTCGACGTAC | GAGGCCAAGA | CCGACACCCT | CAAGAACGCG | 660 |
| CACCTCTCCG | ACATCTGCAT | CAGCACGTCG | GCGGCGCCCA | CCTACTTCCC | GGCGCACTTC | 720 |
| TTCAAGACCG | AGGCCACCGA | CGGCCGGCCC | CCCCGCGAGT | ACCACCTCGT | GGACGGCGGC | 780 |
| GTCGCGGCCA | ACAACCCCAC | CATGGTCGCC | ATGTCCATGC | TCACCAAGGA | GGTGCACCGC | 840 |
| CGCAACCCCA | ACTTCAACGC | CGGCAGCCCC | ACCGAGTACA | CCAACTACCT | CATCATCTCC | 900 |
| GTCGGCACCG | GGTCGGCAAA | GCAGGCGGAG | AAGTACACCG | CGGAGCAGTG | CGCGAAGTGG | 960 |
| GGCCTCATCC | AGTGGCTCTA | CAACGGCGGC | TTCACGCCGA | TCATCGACAT | CTTCTCGCAT | 1020 |
| GCCAGTTCCG | ACATGGTTGA | CATCCATGCG | TCGATCCTCT | TTCAGGCCCT | GCACTGCGAG | 1080 |
| AAGAAGTACC | TTCGCATCCA | GGATGATACT | TTGACTGGGA | ACGCATCGTC | CGTGGACATC | 1140 |
| GCCACCAAGG | AGAACATGGA | GTCTCTGATA | TCGATCGGCC | AGGAGCTGCT | CAAGAAGCCA | 1200 |
| GTGGCGAGAG | TGAACATCGA | CACAGGGGTG | TACGAGTCCT | GCGACGGTGA | GGGCACAAAT | 1260 |
| GCACAGTCGC | TAGCTGACTT | CGCCAAGCAA | CTCTCTGACG | AGCGCAAGCT | ACGCAAGAGC | 1320 |
| AATCTCAACT | CCAACTAATA | AATACCTCTC | TCAGTCACAG | CATGTGCTCT | TTCTGCAGAT | 1380 |
| TCACCGTTTC | TTATTTTTAA | TTTCAATTTC | AATTCAGTGT | ATGTGCGTGT | GTGTGTGACT | 1440 |
| GTACTGTGTG | TACCAATAAA | CATTTAAGTT | CAATCATTTG | CTTGTCTATG | ATCAAAAGAA | 1500 |
| CCATTTCCTT | CTGAAAAAAA | AACGGCACGA | G | | | 1531 |

(2) INFORMATION FOR SEQ ID NO:2:

(i) SEQUENCE CHARACTERISTICS:
        (A) LENGTH: 410 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:2:

```
Met  Gly  Ser  Ile  Gly  Arg  Gly  Thr  Ala  Asn  Cys  Ala  Thr  Val  Pro  Gln
 1             5                   10                  15

Pro  Pro  Pro  Ser  Thr  Gly  Lys  Leu  Ile  Thr  Ile  Leu  Ser  Ile  Asp  Gly
              20                  25                  30

Gly  Gly  Ile  Arg  Gly  Leu  Ile  Pro  Ala  Thr  Ile  Ile  Ala  Tyr  Leu  Glu
             35                  40                  45

Ala  Lys  Leu  Gln  Glu  Leu  Asp  Gly  Pro  Asp  Ala  Arg  Ile  Ala  Asp  Tyr
```

```
                    50                            55                         60
     Phe  Asp  Val  Ile  Ala  Gly  Thr  Ser  Thr  Gly  Ala  Leu  Leu  Ala  Ser  Met
     65                       70                      75                        80

Leu  Ala  Ala  Pro  Asp  Glu  Asn  Asn  Arg  Pro  Leu  Phe  Ala  Ala  Lys  Asp
                         85                      90                      95

Leu  Thr  Thr  Phe  Tyr  Leu  Glu  Asn  Gly  Pro  Lys  Ile  Phe  Pro  Gln  Lys
                    100                      105                     110

Lys  Ala  Gly  Leu  Leu  Thr  Pro  Leu  Arg  Asn  Leu  Leu  Gly  Leu  Val  Arg
               115                      120                     125

Gly  Pro  Lys  Tyr  Asp  Gly  Val  Phe  Leu  His  Asp  Lys  Ile  Lys  Ser  Leu
          130                     135                     140

Thr  His  Asp  Val  Arg  Val  Ala  Asp  Thr  Val  Thr  Asn  Val  Ile  Val  Pro
     145                     150                     155                          160

Ala  Phe  Asp  Val  Lys  Tyr  Leu  Gln  Pro  Ile  Ile  Phe  Ser  Thr  Tyr  Glu
                         165                     170                     175

Ala  Lys  Thr  Asp  Thr  Leu  Lys  Asn  Ala  His  Leu  Ser  Asp  Ile  Cys  Ile
                    180                     185                     190

Ser  Thr  Ser  Ala  Ala  Pro  Thr  Tyr  Phe  Pro  Ala  His  Phe  Phe  Lys  Thr
               195                     200                     205

Glu  Ala  Thr  Asp  Gly  Arg  Pro  Pro  Arg  Glu  Tyr  His  Leu  Val  Asp  Gly
          210                     215                     220

Gly  Val  Ala  Ala  Asn  Asn  Pro  Thr  Met  Val  Ala  Met  Ser  Met  Leu  Thr
     225                     230                     235                          240

Lys  Glu  Val  His  Arg  Arg  Asn  Pro  Asn  Phe  Asn  Ala  Gly  Ser  Pro  Thr
                         245                     250                     255

Glu  Tyr  Thr  Asn  Tyr  Leu  Ile  Ile  Ser  Val  Gly  Thr  Gly  Ser  Ala  Lys
                    260                     265                     270

Gln  Ala  Glu  Lys  Tyr  Thr  Ala  Glu  Gln  Cys  Ala  Lys  Trp  Gly  Leu  Ile
               275                     280                     285

Gln  Trp  Leu  Tyr  Asn  Gly  Gly  Phe  Thr  Pro  Ile  Ile  Asp  Ile  Phe  Ser
          290                     295                     300

His  Ala  Ser  Ser  Asp  Met  Val  Asp  Ile  His  Ala  Ser  Ile  Leu  Phe  Gln
     305                     310                     315                          320

Ala  Leu  His  Cys  Glu  Lys  Lys  Tyr  Leu  Arg  Ile  Gln  Asp  Asp  Thr  Leu
                         325                     330                     335

Thr  Gly  Asn  Ala  Ser  Ser  Val  Asp  Ile  Ala  Thr  Lys  Glu  Asn  Met  Glu
                    340                     345                     350

Ser  Leu  Ile  Ser  Ile  Gly  Gln  Glu  Leu  Leu  Lys  Lys  Pro  Val  Ala  Arg
               355                     360                     365

Val  Asn  Ile  Asp  Thr  Gly  Val  Tyr  Glu  Ser  Cys  Asp  Gly  Glu  Gly  Thr
          370                     375                     380

Asn  Ala  Gln  Ser  Leu  Ala  Asp  Phe  Ala  Lys  Gln  Leu  Ser  Asp  Glu  Arg
     385                     390                     395                          400

Lys  Leu  Arg  Lys  Ser  Asn  Leu  Asn  Ser  Asn
                         405                     410
```